United States Patent [19]

Rothgery et al.

[11] Patent Number: 5,405,971
[45] Date of Patent: Apr. 11, 1995

[54] PREPARATION OF HYDROXYLAMMONIUM SALTS OF 5-NITRO-1,2,4-TRIAZOL-3-ONE

[75] Inventors: Eugene F. Rothgery, North Branford; Francis W. Migliaro, Jr., Waterbury, both of Conn.

[73] Assignee: Olin Corporation, Cheshire, Conn.

[21] Appl. No.: 111,577

[22] Filed: Aug. 25, 1993

Related U.S. Application Data

[62] Division of Ser. No. 878,264, May 4, 1992, Pat. No. 5,274,105.

[51] Int. Cl.6 .......................................... C07D 249/12
[52] U.S. Cl. ................................. 548/263.8; 149/92
[58] Field of Search ........................ 149/92; 548/263.8

[56] References Cited

U.S. PATENT DOCUMENTS

| | | | |
|---|---|---|---|
| H861 | 12/1990 | Collignon et al. | 548/263.8 |
| 3,111,524 | 11/1963 | Wiley et al. | 149/92 |
| 3,607,880 | 9/1971 | Tomita | 548/243 |
| 3,668,873 | 6/1972 | Bauman | 149/36 |
| 3,677,841 | 7/1972 | Ayres et al. | 149/92 |
| 4,028,154 | 6/1977 | Coburn | 149/92 |
| 4,252,965 | 2/1981 | Grace et al. | 548/263 |
| 4,527,389 | 7/1985 | Biddle et al. | 149/75 |
| 4,552,598 | 11/1985 | Lee et al. | 149/92 |
| 4,733,610 | 3/1988 | Lee et al. | 548/263 |
| 4,733,610 | 3/1988 | Lee et al. | 102/332 |
| 4,772,622 | 9/1988 | Britcher et al. | 514/364 |
| 4,958,027 | 9/1990 | Laval et al. | 149/92 |
| 4,968,394 | 11/1990 | Dotson et al. | 204/101 |
| 5,034,072 | 7/1991 | Becuwe | 149/92 |
| 5,223,057 | 6/1993 | Mueller et al. | 149/45 |
| 5,256,792 | 10/1993 | Lee et al. | 548/263.8 |

OTHER PUBLICATIONS

Ritchie, J. Org. Chem., 1989, 54, 3553–3560. (1989).

Dean, "Leage's Handbook of Chemistry", 11th Ed., pp. 4–60, McGraw-Hill Book Co. (1973) New York.

Pevzner et al., J. Org. Chem. of the USSR, 14 (#10) pp. 2024–2029 (Russian), pp. 1877–1881 (English) (1978) (Abstract).

"3-Nitro-1,2,4-Triazol-5-One, A Less Sensitive Explosive", by Kien-Yin Lee and MIchael D. Coburn Crystal Structure of Ammonium 3-Nitro-1,2,4-Triazol-5-Onate, from Propellants, Explosives, Pyrotechnics, 16, 145–146 (1991).

"Synthesis and Initial Characterization of Amine Salts of 3-Nitro-1,2,4-Triazol-5-one", Propellants, Explosives, Pyrotechnics, 14, 241–244 (1989).

Primary Examiner—Edward A. Miller
Attorney, Agent, or Firm—Dale L. Carlson

[57] ABSTRACT

The present invention relates to a novel compound which is the hydroxylammonium or lower alkyl hydroxylammonium salt of 3-nitro-1,2,4-triazol-5-one, together with processes for preparation thereof. One process comprises a two-step reaction comprising: (a) reacting 3-nitro-1,2,4-triazol-5-one with an aqueous alkali metal or alkaline earth metal hydroxide to form an aqueous solution of an alkali metal or alkaline earth metal salt of 3-nitro-1,2,4-triazol-5-one, and (b) reacting said alkali metal or alkaline earth metal salt of 3-nitro-1,2,4-triazol-5-one with an aqueous solution of hydroxylammonium salt or lower alkyl-substituted hydroxylammonium salt to form the hydroxylammonium salt of 3-nitro-1,2,4-triazol-5-one. Another process comprises (a) reacting an aqueous solution of a hydroxylammonium salt or lower alkyl-substituted hydroxylammonium salt with an alkali metal or alkaline earth metal hydroxide to form an aqueous solution of a hydroxylamine free base and (b) reacting said free base with an aqueous solution or slurry of 3-nitro-1,2,4-triazol-5-one at a temperature of between about 5° C. and about 50° C. and at atmospheric pressure.

15 Claims, No Drawings

PREPARATION OF HYDROXYLAMMONIUM SALTS OF 5-NITRO-1,2,4-TRIAZOL-3-ONE

This application is a division of application Ser. No. 07/878,264, filed May 4, 1992, now U.S. Pat. No. 5,274,105.

FIELD OF THE INVENTION

This invention relates generally to hydroxylammonium salts of 5-nitro-1,2,4-triazol-3-one which are useful as relative insensitive energetic compounds in the preparation of explosives and rocket propellants.

BACKGROUND OF THE INVENTION

Up until recent years, high energy explosives and propellants such as 1,3,5-trianitraza cyclohexane ("RDX"), 1,3,5,7-tetranitraza cyclooctane ("HMX"), and trinitrotoluene ("TNT") were considered adequate for weaponry and rocketry applications. However, during the course of the last decade, the problem of unwanted detonation of these high energy explosives and propellants has become of increasing concern to the military.

Thus, the military has had to turn to other, less sensitive materials, such as 3-nitro-1,2,4-triazol-5-one (so-called "NTO"), to provide a greater margin of safety against reaction to unplanned stimuli. NTO exhibits excellent physical properties, including a desired combination of high energy when detonated and relatively low sensitivity to unplanned detonation, making it a current candidate of choice for propellant and explosives applications. Background information on NTO is provided in a technical article by K. Y. Lee and M. D. Coburn entitled "3-Nitro-1,2,4-Triazol-5-One, A Less Sensitive Explosive", Los Alamos National Laboratory (LA-10302-MS, Issued February, 1985), as well as U.S. Pat. No. 4,733,610. Various processes for producing NTO are known in the art, such as, for example, the process disclosed in the above-cited Lee and Coburn article which involves nitrating 1,2,4-triazol-5-one ("TO") by adding solid TO to a mixture containing roughly 60 volume percent of 90 percent nitric acid and 40 volume percent of water. As another illustration, European patent application 210,811, published on Feb. 4, 1987, discloses a process which involves reacting TO with 98 percent nitric acid at relatively low temperatures and with relatively long reaction times. More specifically, this European patent application discloses that TO is added to the 98 percent nitric acid during an addition time of two hours at 5° C. to 10° C., followed by a three hour holding period at ambient temperature, followed by quenching with water at 0° C. and holding for 12 hours. Amine salts of NTO are disclosed in a technical article by K. Y. Lee and M. M. Stinecipher, entitled Synthesis and Initial Characterization of Amine Salts of 3-Nitro-1,2,4-Triazol-5-one published in the journal Propellants, Explosives, Pyrotechnics 14, 241–244 (1989) and the Crystal Structure of Ammonium 3-Nitro-1,2,4-Triazol-5-Onate is described in the same journal in an article by L. Jiarong, C. Boren and O. Yuxiang entitled "Crystal Structure of Ammonium-3-Nitro-1,2,4-Triazol-5-one," 16, 145–146 (1991).

Hydroxylammonium nitrate (so-called "HAN"), which is the nitrate salt of hydroxylamine, is known to be an excellent insensitive oxidizer for propellants, as disclosed, for example, in U.S. Pat. No. 4,968,394 which is more specifically directed to a method for reducing excess nitric acid in aqueous hydroxylamine nitrate solutions.

The need by the military for other insensitive munitions which provide a desired combination of excellent insensitivity and enhanced impetus continues. The present invention provides one answer to that need.

SUMMARY OF THE INVENTION

In one aspect, the present invention relates to a compound which is the hydroxylammonium or lower alkyl hydroxylammonium salt of 3-nitro-1,2,4-triazol-5-one.

In another aspect, the present invention relates to a process for preparing the di-lower alkyl-substituted hydroxylammonium salt of 3-nitro-1,2,4-triazol-5-one by reacting an aqueous solution or slurry of a di-lower alkyl-substituted hydroxylamine with an aqueous solution or slurry of 3-nitro-1,2,4-triazol-5-one at a temperature of between about 5° C. and about 50° C. and at atmospheric pressure.

In another aspect, the present invention relates to a process for preparing the hydroxylammonium salt of 3-nitro-1,2,4-triazol-5-one by a two-step reaction comprising:
 (a) reacting 3-nitro-1,2,4-triazol-5-one with an aqueous alkali metal or alkaline earth metal hydroxide to form an aqueous solution of an alkali metal or alkaline earth metal salt of 3-nitro-1,2,4-triazol-5-one, and
 (b) reacting said alkali metal or alkaline earth metal salt of 3-nitro-1,2,4-triazol-5-one with an aqueous solution of hydroxylammonium salt or lower alkyl-substituted hydroxylammonium salt (preferably nitrate, chloride or sulfate) to form the hydroxylammonium salt of 3-nitro-1,2,4-triazol-5-one.

In still another aspect, the present invention relates to a process for preparing the hydroxylammonium salt of 3-nitro-1,2,4-triazol-5-one by a two-step reaction comprising:
 (a) reacting an aqueous solution of a hydroxylammonium salt or lower alkyl-substituted hydroxylammonium salt (preferably nitrate, chloride or sulfate) with an alkali metal or alkaline earth metal hydroxide to form an aqueous solution of a hydroxylamine free base
 (b) reacting said free base with an aqueous solution or slurry of 3-nitro-1,2,4-triazol-5-one at a temperature of between about 5° C. and about 50° C. and atmospheric pressure.

These and other aspects will become apparent upon reading the following detailed description of the invention.

DETAILED DESCRIPTION OF THE INVENTION

It has now been surprisingly found in accordance with the present invention that hydroxylammonium salts of 3-nitro-1,2,4-triazol-5-one are suitably prepared in excellent yield using the processes of the present invention. The resulting salts provide excellent insensitivity to unwanted detonation, as demonstrated more clearly by the "drop test" results provided in the working examples provided hereinbelow.

In each of the two multi-step processes recited in the "Summary of the Invention" hereinabove, it is preferred that equimolar amounts of reactants are employed in the individual reaction steps. The specified reaction steps are suitably carried out at atmospheric pressure and ambient temperature (preferably between about 15° C. and about 30° C.) although higher or lower temperatures may be employed if desired for some purpose.

In a particularly preferred aspect of the invention, as illustrated by Example 1 hereinbelow, a slurry of aqueous NTO is reacted with aqueous sodium hydroxide to form the sodium salt of NTO which, in turn, is reacted with aqueous hydroxylammonium nitrate. Upon standing, the desired hydroxylammonium salt of NTO precipitates out to provide a high purity product.

As more fully illustrated by the working examples provided hereinbelow, further product purification is suitably effected as desired using well-known recrystallization techniques in a suitable solvent, such as acetonitrile (see Examples 3 and 4 hereinbelow) or a solvent/non-solvent pair, such as ethanol/water (see Example 2 hereinbelow). As demonstrated by Examples 5 and 6 hereinbelow, the hydroxylammonium salts produced in accordance with the present invention provide excellent impact insensitivity as compared to RDX and conventional insensitive munitions such as triaminoguanidine nitrate ("TAGN"), as well as excellent impetus values.

EXAMPLE 1

Preparation of Hydroxylammonium Salt of 3-Nitro-1,2,4-Triazol-5-one (HANTO)

To a slurry of NTO (2.6 g, 0.02 mole) in 85 ml of water was added 50% NaOH solution (1.6 g, 0.02 mole). A bright yellow solution formed. To this was added an 81% hydroxylammonium nitrate solution (2.25 g, 0.02 mole). On standing a yellow solid fell from solution. It was isolated by filtration and dried on a porous plate. Obtained were 1.5 g melting at 188°–190° C. with decomposition.

Elemental Analysis: Calculated: C,14.71; H,3.09; N,42.94. Found: C,14.85; H,3.40; N, 42.95 DSC Results: Exothermic decomposition peaks at 190° C. and at 270° C.

EXAMPLE 2

Alternate Preparation of Hydroxylammonium Salt of 3-Nitro-1,2,4-Triazol-5-one (HANTO)

Hydroxylammonium sulfate (1.64 g, 0.02 eq.) was dissolved in 10 ml of water. To this was added 50% NaOH solution (1.6 g, 0.02 mole). This solution was poured into a slurry of NTO (2.6 g, 0.02 mole) in 10 ml of water. A yellow solution forced immediately. On stirring a yellow solid precipitated. Filtering and washing with ice water gave 3.3 g of wet cake. This material was recrystallized from ethanol/water to give a product melting at 188° C. with decomposition.

EXAMPLE 3

Preparation of Diethylhydroxylammonium Salt of 3-Nitro-1,2,4-Triazol-5-one (DEHANTO)

NTO (2.6 g, 0.02 mole) was slurried in 25 ml of methanol. To this was added diethylhydroxylamine (1.84 g, 0.021 mole). A yellow color developed immediately and on further stirring a clear, yellow solution resulted. The solvent was partially evaporated with the formation of a pale yellow solid. Obtained on filtering was 4.4 of crude product. Recrystallization from acetonitrile gave a product melting at 108°–110° C. without apparent decomposition.

Elemental Analysis: Calculated: C,32.89; H,5.98; N,31.95. Found: C,33.15; H,6.75; N,32.15

EXAMPLE 4

Methylhydroxylammonium Salt of 3-Nitro-1,2,4-Triazol-5-one (MHANTO)

N-methylhydroxylammonium chloride (1.67 g, 0.02 mole) was dissolved in 10 ml of water. To this solution was added 50% NaOH solution (1.60 g, 0.02 mole). The resulting solution was poured into a slurry of NTO (2.6 g, 0.02 mole) in 20 ml of water. An intense yellow color resulted. An additional 10 ml of water was added to give a clear, yellow solution, which was stirred for 15 minutes. The solvent water was removed under vacuum to leave a yellow solid. The solids were extracted with acetonitrile. An additional recrystallization from acetonitrile gave a product melting with decomposition at 157-8° C.

Elemental Analysis: Calculated: C,20.33; H,3.95; N,39.54. Found: C,20.7; H,4.15; N,39.45 DSC Results: Exothermic decomposition at 141° C.

EXAMPLE 5

Impact Sensitivity

One of the critical measures of the insensitivity of an energetic compound is its impact sensitivity as measured by dropping a weight on a sample of the material using, in this case, a 2 kg weight. The tests were performed using a Bureau of Mines apparatus.

|  | Material | Height (cm) |
| --- | --- | --- |
| Comp. Ex. | NTO | >200 |
|  | TAGN | 200 |
|  | RDX | 110 |
|  | HANTO | >200 |
|  | DEHANTO | >200 |

EXAMPLE 6

Blake Gun Code Evaluations

The performance of the pure materials was evaluated using the Blake Thermodynamic Code. This is a program developed by the U.S. Army for the evaluation of materials for use in gun applications. It accurately predicts the parameters of interest to ballisticians such as energy (impetus), flame temperature, pressure and exhaust gas content as well as other thermodynamic values.

|  | Material | Impetus (J/g) |
| --- | --- | --- |
| Comp. Ex. | ANTO | 642 |
|  | HNTO | 798 |
|  | TAGNTO | 836 |
|  | HANTO | 914 |

ANTO = Ammonium salt of NTO
HNTO = Hydrazinium salt of NTO
TAGNTO = Triaminoguanidinium salt of NTO
HANTO = Hydroxylammonium salt of NTO While the invention has been described, above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. A process for preparing a di-lower alkyl-substituted hydroxylammonium salt of 3-nitro-1,2,4-triazol-5-one by reacting an aqueous solution or slurry of a di-lower alkyl-substituted hydroxylamine with an aqueous solution or slurry of 3-nitro-1,2,4-triazol-5-one at a temperature of between about 5° C. and about 50° C. and at atmospheric pressure.

2. The process of claim 1 wherein said di-lower alkyl is dimethyl.

3. The process of claim 1 wherein said di-lower alkyl is diethyl.

4. The process of claim 1 wherein said di-lower alkyl is dipropyl.

5. The process of claim 1 which comprises reacting equimolar amounts of said di-lower alkyl-substituted hydroxylamine relative to said 3-nitro-1,2,4-triazol-5-one.

6. A process for preparing a hydroxylammonium salt of 3-nitro-1,2,4-triazol-5-one by a two-step reaction comprising:
   (a) reacting 3-nitro-1,2,4-triazol-5-one with an aqueous alkali metal or alkaline earth metal hydroxide to form an aqueous solution of an alkali metal or alkaline earth metal salt of 3-nitro-1,2,4-triazol-5-one, and
   (b) reacting said alkali metal or alkaline earth metal salt of 3-nitro-1,2,4-triazol-5-one with an aqueous solution of hydroxylammonium salt or lower alkyl-substituted hydroxylammonium salt to form the respective hydroxylammonium or lower alkyl-substituted hydroxylammonium salt of 3-nitro-1,2,4-triazol-5-one.

7. The process of claim 6 wherein step (b) is effected using a lower alkyl-substituted hydroxylammonium salt wherein said alkyl is methyl or dimethyl.

8. The process of claim 6 wherein step (b) is effected using a lower alkyl-substituted hydroxylammonium salt wherein said alkyl is ethyl or diethyl.

9. The process of claim 6 wherein step (a) is effected using an equimolar amount of said 3-nitro-1,2,4-triazol-5-one relative to said alkali metal or alkaline earth metal hydroxide and wherein step (b) is effected using an equimolar amount of said alkali metal or alkaline earth metal salt of 3-nitro-1,2,4-triazol-5-one relative to said hydroxylammonium salt or lower alkyl-substituted hydroxylammonium salt.

10. The process of claim 6 wherein said hydroxylammonium salt or lower alkyl-substituted hydroxylammonium salt is selected from the group consisting of nitrate, chloride and sulfate salts.

11. A process for preparing a hydroxylammonium salt of 3-nitro-1,2,4-triazol-5-one by a two-step reaction comprising:
   (a) reacting an aqueous solution of a hydroxylammonium salt or lower alkyl-substituted hydroxylammonium salt with an alkali metal or alkaline earth metal hydroxide to form an aqueous solution of a hydroxylamine free base
   (b) reacting said free base with an aqueous solution or slurry of 3-nitro-1,2,4-triazol-5-one at a temperature of between about 5° C. and about 50° C. and at atmospheric pressure.

12. The process of claim 11 wherein step (a) is effected using a lower alkyl-substituted hydroxylammonium salt wherein said alkyl is methyl or dimethyl.

13. The process of claim 11 wherein step (a) is effected using a lower alkyl-substituted hydroxylammonium salt wherein said alkyl is ethyl or diethyl.

14. The process of claim 11 wherein step (a) is effected using an equimolar amount of said hydroxylammonium salt or lower alkyl-substituted hydroxylammonium salt relative to said alkali metal or alkaline earth metal hydroxide and wherein step (b) is effected using an equimolar amount of said free base relative to said 3-nitro-1,2,4-triazol-5-one.

15. The process of claim 11 wherein said hydroxylammonium salt or lower alkyl-substituted hydroxylammonium salt is selected from the group consisting of nitrate, chloride and sulfate salts.

* * * * *